United States Patent [19]

Fauran et al.

[11] 4,122,202

[45] Oct. 24, 1978

[54] AMINO-3H-ISOBENZOFURANONES N-SUBSTITUTES AND THEIR THERAPEUTIC APPLICATION

[75] Inventors: Francois Fauran, Castanet-Tolosan; Claude Feniou, Pessac; Annie Thibault, Le Bouscat; Gisele Prat, Talence, all of France

[73] Assignee: Societe Cortial, Paris, France

[21] Appl. No.: 703,602

[22] Filed: Jul. 8, 1976

[30] Foreign Application Priority Data

Jul. 9, 1975 [FR] France ................................. 75 21504
Jul. 1, 1976 [FR] France ................................. 76 20048
Jul. 1, 1976 [FR] France ................................. 76 20049

[51] Int. Cl.² .................. A61K 31/335; C07D 319/08; C07D 317/44; A61K 31/36
[52] U.S. Cl. .................. 424/278; 260/340.3; 260/340.5 R; 424/282
[58] Field of Search .................. 260/340.3, 340.5; 424/278, 282

[56] References Cited

U.S. PATENT DOCUMENTS 3,862,176   1/1975   Fauran et al. .................. 424/282 X

FOREIGN PATENT DOCUMENTS 46M     1/1960   France ................................. 424/278
83,649  3/1954   Norway ........................... 260/340.5 R

OTHER PUBLICATIONS

Chem. Abstracts: 58:12612e; 78:P43460c; 83:206050p.

*Primary Examiner*—Ethel G. Love
*Attorney, Agent, or Firm*—Oblon, Fisher, Spivak, McClelland & Maier

[57] ABSTRACT

3-Amino 3H-isobenzofuranones substituted on the nitrogen atom with benzodioxol-1,3, benzodioxane-1,4 or benzodioxane-1,3 rings are described which possess analgesic and anti-edematous properties.

9 Claims, No Drawings

AMINO-3H-ISOBENZOFURANONES N-SUBSTITUTES AND THEIR THERAPEUTIC APPLICATION

This invention relates to N-substituted, 3-amino 3H-isobenzofuranones-1 which are useful as medicinal agents.

The compounds of the present invention are represented by the following formula

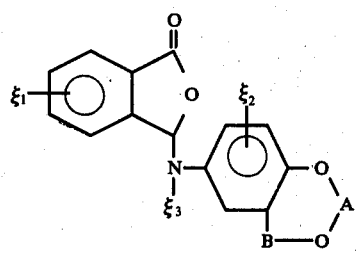

wherein $\xi_1$ is H or at least one substituent preferably selected from the group of OH, OMe, and OCOCH$_3$, or

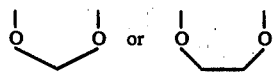

attached to two contiguous carbons of the benzene ring; $\xi_2$ is H or at least one substituent preferably selected from lower alkyl groups of C$_1$-C$_4$ carbon atoms, COOCH$_3$ or COOH and its salts of pharmacologically compatible bases; $\xi_3$ is H or a lower alkyl of C$_1$-C$_4$ carbon atoms or benzyl;

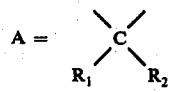

with R$_1$ and R$_2$ the same or different and selected from the group of H, lower alkyl of C$_1$-C$_4$ carbon atoms, aryl, arylalkyl, and cycloalkyl or R$_1$ and R$_2$ form, with contiguous carbon atoms, an alicyclic group comprising at most 7 carbon atoms, or A is

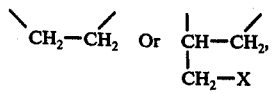

wherein X is halogen, OH, OCOCH$_3$, OCH$_2$CH$_2$N⟨ ⟩,

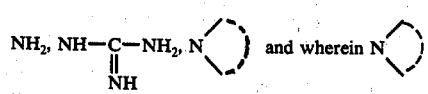

represents a secondary or tertiary, cyclic or acyclic, amine function; B is a simple bond or

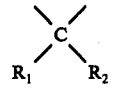

wherein R$_1$ and R$_2$ are as defined above with the proviso in the last case that $\xi_2$ be selected from the substituents of H or lower alkyl of C$_1$-C$_4$ carbon atoms and that A be selected from the groups of

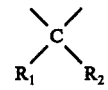

with R$_1$ and R$_2$ as defined above.

The products of the invention are novel compounds and are useful therapeutically because of their analgesic and anti-edematous effects.

The compounds of the present invention are generally obtained by a reaction in which 2-formyl benzoic acid or a derivative thereof, having formula II and an amine of formula III are reacted in an appropriate solvent such as benzene.

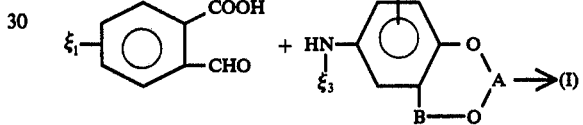

The derivatives of formula III such as

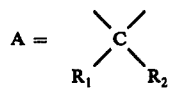

wherein R$_1$ and R$_2$ differ from H and B is a simple bond are generally prepared in the first stage by a reaction between catechol compound (IV) and a ketone or an aldehyde (V) in the presence of P$_2$O$_5$ or paratoluenesulfonic acid in benzene

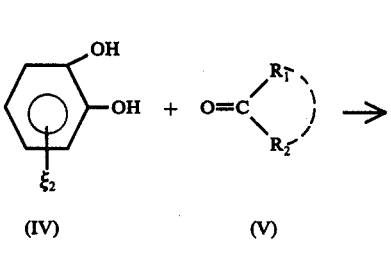

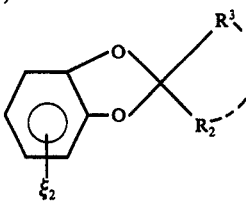

The carbonyl derivative (V) can be replaced by a gem-dihalogenated derivative. In the case where $R_1 = R_2 = H$, the derivative (V) can be replaced by methylene chloride. The products of formula (VI) are then nitrated and finally reduced by means of known methods whereby the amines of formula (III) such as $\xi_3 = H$ are obtained. The N-alkylated derivatives are prepared from primary amines by utilizing, for example, the method described by Hideo Agui and co-workers in J. Heterocycl. Chem., 1971, 8, 357–65. The derivatives such as

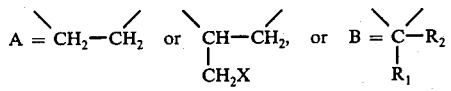

are prepared by means of similar methods.

Having generally described the invention, a more complete understanding can be obtained by reference to certain specific examples, which are included for purposes of illustration only and are not intended to be limiting unless otherwise specified.

Example 1 — N(2,2-dimethyl benzodioxol-1,3 yl-5) 3-amino 3H-isobenzofuranones In a three-necked balloon flask, a mixture of 10 g of catechol and 10 ml of dry acetone was heated to 60° C. 16 g $P_2O_5$ were added in portions over a period of 15 minutes. The mixture was then agitated and heated for one hour. A solution of 5% soda was added to the reactive cooled mixture in order to make the solution slightly basic. By means of distillation with steam, 3.5 g of 2,2-dimethyl benzodioxol-1,3 (Yield 26%) BP+ 760 = 182° C were obtained.

2,2-Dimethyl benzodioxol-1,3 (5.4 g) was placed into suspension in a solution of 5.5 g of sodium nitrite in 150 ml water. A 25 ml amount of 2.5 M sulphuric acid solution was added, within 5 minutes to the reaction mixture which was cooled to 0° C. After extraction with ether, washing with water, drying of the organic phases and evaporation of the ether, distillation of the 5-nitro 2,2-dimethyl benzodioxol-1,3 was effected. A 4.2 g amount of this derivative was dissolved in a mixture in a 1:1 ratio of ethanol and ethyl acetate and subjected to hydrogenation in the presence of Raney nickel. After filtration of the nickel and evaporation of the solvent, distillation under nitrogen was effected. In this manner, 5-amino 2,2-dimethyl benzodioxol-1,3 was obtained. BP+0.08 mm Hg 88° C.

A 15 g amount of 2-formyl benzoic acid and 18 g of 5-amino 2,2-dimethyl benzodioxol-1,3 were mixed in 500 ml of anhydrous benzene. This mixture was brought to reflux and water was gradually eliminated as it formed by means of a Dean-Stark trap. The reaction was complete after two hours. It was left to cool and the precipitate, which had formed, was filtered and then was recrystallized in benzene. In this way, about 23 g of N(2,2-dimethyl benzodioxol-1,3 yl-5) 3-amino 3H-isobenzofuranone-1 were obtained. (Yield approximately 80%).

Example II — (oxo-1 3H-isobenzofuranyl-3 amino)-5 spiro [(benzodioxol-1,3)-2, 1'cyclohexane].

In a three-necked balloon flask provided with a Dean-Stark trap, which is a device which allows the elimination of water which forms during the course of a reaction, a mixture of 10 g of catechol, 20 g of cyclohexanone, 2 g of sulfonic paratoluene acid and 500 ml of benzene was brought to reflux. After 24 hours, the benzene was evaporated and then the residue was distilled under vacuum. In this way, spiro [(benzodioxol-1,3)-2, 1'-cyclohexane] was obtained. Boiling point under 0.25 mm mercury—90° C. Yield of the reaction 60%.

A 7 g amount of spiro [(benzodioxol-1,3)-2, 1'-cyclohexane] was placed in suspension in a solution of 5.5 g of sodium nitrite in 500 ml of water. A 25 ml solution of 2.5 M sulfuric acid was added, within five minutes, to the reactive mixture which was cooled to 0° C. After extraction with ether, washing with water, drying of the organic phases and evaporation of the ether, the distillation of 5-nitro spiro [(benzodioxol-1,3)-2, 1'-cyclohexane] was effected.

A 5 g amount of the nitro-derivative was dissolved in a mixture of a 1:1 ratio of ethanol and ethyl acetate and was subjected to hydrogenation in the presence of Raney nickel. After filtration of the nickel and evaporation of the solvent, distillation under nitrogen was effected. In this way, 5-amino spiro [(benzodioxol-1,3)-2, 1'cyclohexane] was obtained. Boiling point at a pressure of 0.2 mm mercury of 114° C. F: 60° C.

A 15 g amount of 2-formyl benzoic acid and 22 g of 5-amino spiro [benzodioxol-1,3)-2 1' cyclohexane] were mixed in 500 ml of anhydrous benzene and the mixture was brought to reflux. The water was eliminated as it formed by a Dean-Stark trap. After 2 hours, the solution was left to cool. The precipitate was filtered and recrystallized in benzene. The yield of (1-oxo 3H-isobenzofuranyl-3 amino)-5 spiro[(benzodioxol-1,3)-2, 1' cyclohexane] obtained was about 80%.

Example III — N(6-methyl benzodioxol-1,3 yl-5) 3-amino 3H-isobenzofuranone-1.

In a three-necked balloon flask equipped with an agitator and a refrigerant, 60 g of 4-methyl catechol and 50 g of methylene chloride were dissolved in 750 ml of dimethylsulfoxide. A 40 g amount of pulverized soda was added under nitrogen. The mixture was heated for 2 hours at reflux to 120° C. The 5-methyl benzodioxol-1,3 was obtained by distillation with steam. The yield was 70%.

To 1 liter of nitric acid with a density of 1.20, 150 mg of 5-methyl benzodioxol-1,3 were added drop by drop over a period of 1 hour with stirring and by maintaining the temperature at 25° - 30° C. Stirring was continued for two hours. The 5-nitro 6-methyl benzodioxol-1,3 was filtered. The yield of product from the nitration reaction was 98%.

The nitrated crude derivative was subjected to hydrogenation over Raney nickel in the ethanol-ethyl acetate mixture. The nickel was removed by filtration, and the solvent was evaporated. The 5-amino 6-methyl benzodioxole-1,3 was distilled. The yield of the reducing reaction was 95%. P.F.: 94° C.

The mixture of 15 g of 2-formyl benzoic acid and of 15 g of 5-amino 6-methyl benzodioxole-1,3 in 500 ml of anhydrous benzene was brought to reflux. The water was eliminated as it formed by means of a Dean-Stark trap. After two hours, the mixture was left to cool and the precipitate, which had formed, was filtered and then was recrystallized in benzene. The yield of the reaction product was 80%.

Example IV — N(benzodioxol-1,3 yl-5) 3-amino 6,7-dimethoxy 3H-isobenzofuranone A mixture of 10 g of 2,3-dimethoxy benzoic acid, 25 ml of a 37% formaldehyde solution and 40 ml of concentrated hydrochloric acid was heated to 70° C until complete dissolution was achieved. The solution was filtered while hot, cooled and diluted with 100 ml of water. 6,7-Dimethoxy 3H-isobenzofuranone-1 precipitated. After filtration, 3 g of the material was recovered.

A mixture of 20 g of 6,7-dimethoxy 3H-isobenzofuranone-1, 1.2 l of ethanol and 500 ml of dimethylamine was agitated for a period of 15 hours at ambient temperature. After evaporation, about 21 g of the N,N-dimethylamide of 2-hydroxymethyl 6,7-dimethoxy benzoic acid were obtained. Yield approximately 89%.

A 1g amount of this product was taken up in 220 ml of acetic acid. 11 g of chromic anhydride, 11 ml of water, and 220 ml of acetic acid were added to this solution. The mixture was agitated for 7 minutes and then diluted by 1.1 liter of water. The aqueous phase was extracted four times with 0.4 l of chloroform. The chloroform phase was washed until it was neutral, and then dried. The chloroform was eliminated by evaporation. The residue was again taken up by 150 ml of 3N hydrochloric acid. The mixture was brought to reflux for two hours. After cooling, 2-formyl 6,7-dimethoxy benzoic acid was obtained which was recrystallized in water. The yield of the reaction product was 46%.

The condensation of the 2-formyl 6,7-dimethoxy benzoic acid with 5-amino benzodioxol-1,3 was effected by means of the customary, already described methods. The yield of the reaction product was 80%.

Example V — SYNTHESIS OF 3-[N(BENZODIOXAN-1,4 YL-6) AMINO] 6,7-DIMETHOXY 3H-ISOBENZOFURANONE A mixture of 30 g of 6,7-dimethoxy 3H-isobenzofuranone, prepared according to the method described in Example IV, 1 liter of ethanol and 300–400 cm³ of dimethylamine was agitated for several hours and then evaporated under vacuum at 30° - 35° C. The crystallized product was washed with heptane. The 2,3-dimethoxy N,N-dimethyl 6-hydroxymethyl benzamide was obtained in a yield of 100%. F = 90° C.

33 g of chromic anhydride were dissolved in 33 cm³ water. 660 cm³ of CH₃COOH were added to this solution. The obtained mixture was poured into a balloon flask containing 33 g of the amide which had been previously prepared in 660 cm³ RP acetic acid. The mixture was agitated for 7 minutes.

A 3.3 l amount of water was added and the mixture was extracted 4 times with 1 liter of chloroform. The chloroform solution was washed with water and then by a 10% soda bicarbonate solution until neutralized, dried over Na sulfate and then evaporated. A 330 cm³ amount of a 3 N HCl solution was added to the residue. The mixture was brought to reflux for 2 hours; dimethoxy-5 phthalaldehydric acid crystallized upon cooling of the solution. It was recrystallized from water, and obtained in a yield of 40 - 50%. F = 149° C.

A 20 g amount of this acid was suspended in 1.5 l of benzene in a balloon flask under magnetic agitation. 0.11 mole of benzodioxan-1,4 yl-6 amine, dissolved in a small quantity of benzene, was added to the mixture which was brought to 110° C. The water which formed in the course of the reaction was removed by azeotropic distillation.

After filtration, (N-benzodioxan-1,4 yl-6) 3-amino 6,7-dimethoxy 3H-isobenzofuranone was recrystallized from benzene. F = 190° C.

Example VI — SYNTHESIS OF THE N-(ACETOXYMETHYL-2 AND -3 BENZODIOXAN-1,4 YL-6) 3-AMINO 3H-ISOBENZOBURANONES.

To 110 g of pyrocatechol, was added a solution of 40 g of soda in 400 cm³ water and then 3 moles of 1-chloro 2,3-epoxy propane. The mixture was heated to 100° C for 4 hours, then cooled and extracted with ether. The ether phase was washed several times by a 3% soda solution, then to neutrality, dried with sodium sulfate and evaporated. 2-Hydroxymethyl benzodioxan-1,4 was recrystallized in methanol, and was obtained in a yield of 85%. F = 86° C.

A 400 cm³ amount of acetic anhydride and a drop of sulfuric acid were added to 80 g of the alcohol. The mixture was heated for 3 hours to 100° C. It was then poured into 3 l of ice water, dried, evaporated and distilled. The acetic ester of the 2-hydroxymethyl benzodioxane was obtained in a yield of 75%, boiling point — 0.1 mm Hg = 110° C. 17 g of the ester were dissolved in 100 cm³ of acetic acid. A 7.5 g amount of HNO₃ (d = 1.50) diluted in 100 cm³ acetic acid was added to this solution. All of it was heated to 100° C. for 45 minutes. The mixture was poured into cold water and extracted with chloroform. The chloroform phase was dried and then evaporated.

A 100 cm³ amount of diluted hydrochloric acid was added to the residue. The mixture was heated to 100° C for 3 hours, poured into water and extracted with chloroform. The chloroform phase was washed with water, dried and evaporated. Benzene was added and the solution was evaporated again. The obtained solid melted at 100° - 110° and consisted of a mixture of two derivatives, 6- and 7-nitro (hydroxymethyl)-2 benzodioxane-1,4. The finely crushed solid was suspended in 150 cm³ CHCl₃. The solution was agitated for 2 hours and then filtered. A white-colored precipitate was obtained with a melting point of F = 134° C which was 2-hydroxymethyl 7-nitro benzodioxane-1,4. The filtrate contained 2-hydroxymethyl 6-nitro benzodioxane-1,4 of yellow color which was crystallized with F = 124° C.

The two products distinguished themselves by their very characteristic IR bands

| 6-nitro F = 124° C | 7-nitro F = 134° C |
|---|---|
| 930 cm⁻¹ | |
| 780 cm⁻¹ | 970 cm⁻¹ |
| 690 cm⁻¹ | |

These products were then separately acetylated, reduced to the corresponding amine and condensed with phthalic aldehyde according to the known methods in order to obtain the corresponding 3-amino 3H-isobenzofuranones.

Example VII — SYNTHESIS OF THE (N-BENZODIOXANE-1,3 YL-6) 3-AMINO 3H-ISOBENZOFURANONE A 20 g amount of p-nitrophenol was dissolved in 24 cm³ of a 40% formaldehyde solution by slightly heating it. A 60 cm³ amount of diluted sulfuric acid was poured into this solution which solidified immediately. After filtration and washing with water to a pH of 7, the 6-nitro benzodioxane-1,3 was recrystallized in hot 95° alcohol. It was obtained in a yield of 63%. F = 145° C.

A 30 g amount of the nitrated derivative was dissolved in ethyl acetate. After having added Raney nickel, a hydrogen current was passed through the solution until complete reaction was achieved. It was filtered, evaporated and then distilled in order to obtain 75% of 6-amino benzodioxane-1,3; F = 64° C.

A 24.75 g amount of phthalaldehydic acid was brought to reflux in 500 cm³ and 0.15 mole of amine dissolved in benzene was added to this solution. In the course of the reaction, the final product precipitated. It was filtered while hot and had a melting point of 188° C.

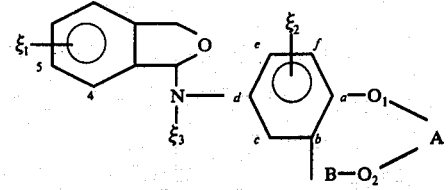

Table No. 1 indicates the melting points of products of this invention

| PRODUCTS | $\xi_1$ | $\xi_2$ | $\xi_3$ | $(O_2)\diagdown\diagup(O_1)$ A | B | MP (° C) |
|---|---|---|---|---|---|---|
| 1 | H | H | H | >C< H,H | — | 180 |
| 2 | H | H | H | >C< Et,Et | — | 187 |
| 3 | H | H | H | cyclohexyl | — | 186 |
| 4 | H | H | H | >C< Pr,Pr | — | 152 |
| 5 | H | H | H | >C< Me,Bu | — | 120 |
| 6 | H | H | H | >C< Et,Pr | — | 168 |
| 7 | H | H | H | >C< Me,Me | — | 198 |
| 8 | OMe-6, OMe-7 | H | H | >C< H,H | — | 210 |
| 9 | H | Me-e | H | >C< H,H | — | 176 |
| 10 | H | H | H | benzo (indane) | — | 178 |
| 11 | H | H | H | cyclohexyl | — | 200 |
| 12 | H | H | Et | >C< H,H | — | 92 |
| 13 | H | H | H | $CH_2\!-\!CH_2$ | — | 156 |
| 14 | OMe-6, OMe-7 | H | H | $CH_2\!-\!CH_2$ | — | 190 |

-continued

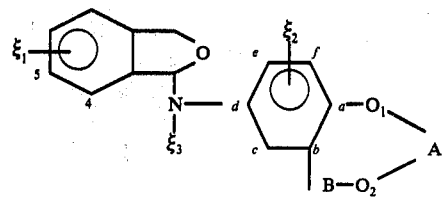

Table No. 1 indicates the melting points of products of this invention

| PRODUCTS | $\xi_1$ | $\xi_2$ | $\xi_3$ | $(O_2)\diagdown\diagup(O_1)$ A | B | MP (° C) |
|---|---|---|---|---|---|---|
| 15 | H | COOH-e | H | $\diagdown CH_2 \diagup$ | — | 260 |
| 16 | H | COOMe-e | H | $\diagdown CH_2 \diagup$ | — | 270 |
| 17 | H | H | H | $\diagdown CH_2-CH \diagup$ <br> $\quad\quad\;\; \mid$ <br> $\quad\quad\;\; CH_2OH$ | — | 171 |
| 18 | H | H | H | $\diagdown CH-CH_2 \diagup$ <br> $\quad\; \mid$ <br> $\quad\; CH_2OH$ | — | 126 |
| 19 | H | H | H | $\diagdown CH-CH_2 \diagup$ <br> $\quad\; \mid$ <br> $\quad\; CH_2OCOMe$ | — | 141 |
| 20 | H | H | H | $\diagdown CH_2-CH \diagup$ <br> $\quad\quad\;\; \mid$ <br> $\quad\quad\;\; CH_2OCOMe$ | — | 146 |
| 21 | H | H | H | $\diagdown CH_2 \diagup$ | $\diagdown CH_2 \diagup$ | 188 |
| 22 | H | Me-c Me-f | H | $\diagdown CH_2 \diagup$ | $\diagdown CH_2 \diagup$ | 171 |

The physico-chemical data are completed by the NMR spectra of each sample in DMSO D6 (internal TMS reference).

In the following formulas, equivalent protons are represented by the same letter. The aromatic protons of the same ring, even though not equivalent, are also represented by the same letter.

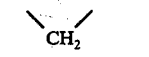

| a | singlet | 5,9 ppm | 2 protons |
|---|---|---|---|
| b + c + d | massif complex | 6,2–7,4 ppm | 5 protons |
| e | massif complex | 7,8 ppm | 4 protons |

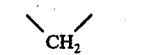

| a | triplet | 0,9 ppm | 6 protons |
|---|---|---|---|
| b | quadruplet | 1,8 ppm | 4 protons |
| c + d + e | massif complex | 6,1–7,4 ppm | 5 protons |
| f | massif complex | 7,7 ppm | 4 protons |

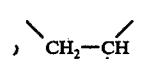

| a | massif complex | 1,7 ppm | 10 protons |
|---|---|---|---|
| b + c + d | massif complex | 6,1–7,4 ppm | 5 protons |
| e | massif complex | 7,7 ppm | 4 protons |

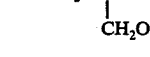

| a + b + c | massif complex | 0,6–2,3 ppm | 14 protons |
|---|---|---|---|
| e + d + f | massif complex | 6,1–7,4 ppm | 5 protons |
| g | massif complex | 7,7 ppm | 4 protons |

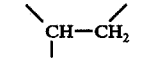

| a + b + c + d | massif complex | 0,6–2,2 ppm | 12 protons |
|---|---|---|---|
| e + f + g | massif complex | 6,4–7,4 ppm | 5 protons |

-continued

| | | | |
|---|---|---|---|
| h | massif complex | 7,7 ppm | 4 protons |

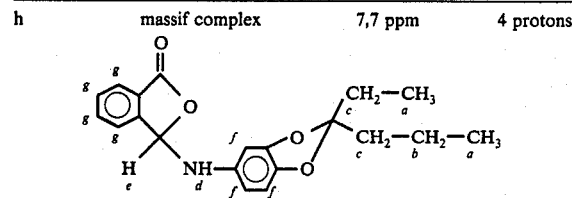

| | | | |
|---|---|---|---|
| a | triplet | 0,9 ppm | 6 protons |
| b + c | massif complex | 1,1-2,2 ppm | 6 protons |
| d + e + f | massif complex | 6,1-7,4 ppm | 5 protons |
| g | massif complex | 7,7 ppm | 4 protons |

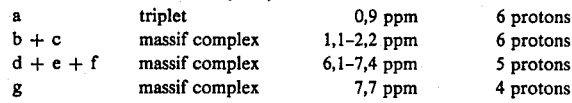

| | | | |
|---|---|---|---|
| a | singlet | 1,6 ppm | 6 protons |
| b + c + d | massif complex | 6,2-7,4 ppm | 5 protons |
| e | massif complex | 7,7 ppm | 4 protons |

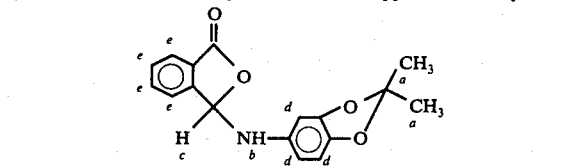

| | | | |
|---|---|---|---|
| a | singlet | 3,9 ppm | 6 protons |
| b | massif complex | 5,9 ppm | 2 protons |
| c + d + e | massif complex | 6,1-7,1 ppm | 5 protons |
| f | massif complex | 7,4 ppm | 2 protons |

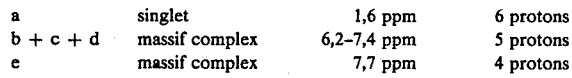

| | | | |
|---|---|---|---|
| a | singlet | 2,1 ppm | 3 protons |
| b | singlet | 5,9 ppm | 2 protons |
| c + d + e + f | massif complex | 6,1-8,0 ppm | 8 protons |

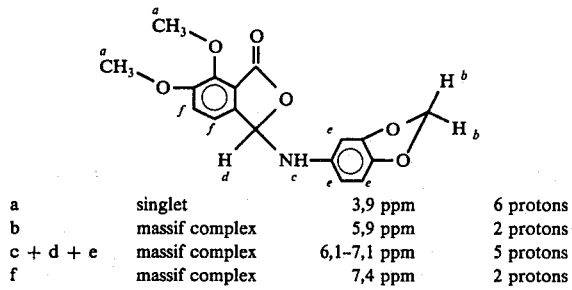

| | | | |
|---|---|---|---|
| a | triplet | 0,9 ppm | 3 protons |
| b | quadruplet | 3,1 ppm | 2 protons |
| c | singlet | 5,9 ppm | 2 protons |
| d + e | massif complex | 6,5-7,1 ppm | 4 protons |
| f | massif complex | 7,7 ppm | 4 protons |

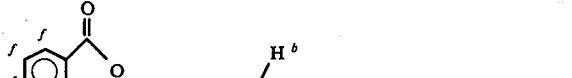

| | | | |
|---|---|---|---|
| a | singlet | 4,2 ppm | 4 protons |
| b + c + d | massif complex | 6,2-7,4 ppm | 5 protons |
| e | massif complex | 7,7 ppm | 4 protons |

-continued

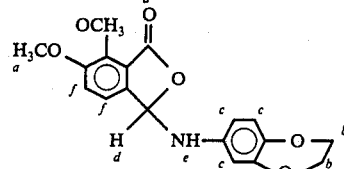

| | | | |
|---|---|---|---|
| a | singlet | 3,9 ppm | 6 protons |
| b | singlet | 4,2 ppm | 4 protons |
| c + d + e | massif complex | 6,7-7,1 ppm | 5 protons |
| f | massif complex | 7,4 ppm | 2 protons |

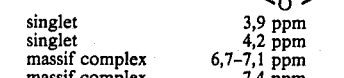

| | | | |
|---|---|---|---|
| a + c | singlet | 6,1 ppm | 2 protons |
| b + c | massif complex | 6,9-7,4 ppm | 3 protons |
| d | massif complex | 7,5-8,1 ppm | 4 protons |
| e | massif complex | 8,9 ppm | 1 proton |
| f | dôme | 12,6 ppm | 1 proton |

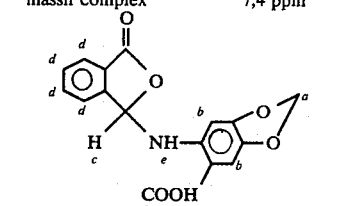

| | | | |
|---|---|---|---|
| a + b + c | massif complex | 3,4-4,5 ppm | 5 protons |
| d + e + f + g | massif complex | 5,5-7,4 ppm | 6 protons |
| h | massif complex | 7,4-8,1 ppm | 4 protons |

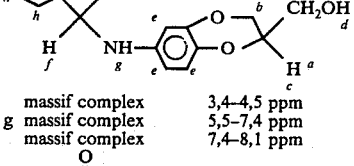

| | | | |
|---|---|---|---|
| a + b + c | massif complex | 3,4-4,4 ppm | 5 protons |
| d | dôme | 5,1 ppm | 1 proton |
| e + f + g | massif complex | 6,3-7,4 ppm | 5 protons |
| h | massif complex | 7,5-8 ppm | 4 protons |

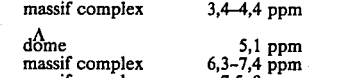

| | | | |
|---|---|---|---|
| a | singlet | 2,1 ppm | 3 protons |
| b + c + d | massif complex | 3,7-4,6 ppm | 5 protons |
| e + f + g | massif complex | 6,3-7,3 ppm | 5 protons |
| h | massif complex | 7,4-8,1 ppm | 4 protons |

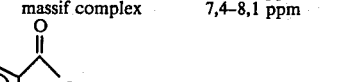

| | | | |
|---|---|---|---|
| a | singlet | 2,1 ppm | 3 protons |
| b + c + d | massif complex | 3,7-4,6 ppm | 5 protons |
| e + f + g | massif complex | 6,3-7,3 ppm | 5 protons |
| h | massif complex | 7,4-8 ppm | 4 protons |

-continued

| | | | |
|---|---|---|---|
| a | singlet | 4,9 ppm | 2 protons |
| b | singlet | 5,2 ppm | 2 protons |
| c + d + e | massif complex | 6,5–7,4 ppm | 5 protons |
| f | massif complex | 7,4–8,1 ppm | 4 protons |

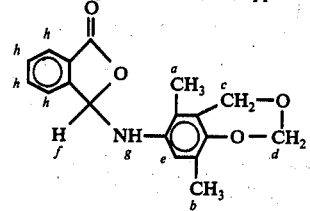

| | | | |
|---|---|---|---|
| a | singlet | 2 ppm | 3 protons |
| b | singlet | 2,2 ppm | 3 protons |
| c | singlet | 4,8 ppm | 2 protons |
| d | singlet | 5,2 ppm | 2 protons |
| e + f + g + h | massif complex | 6,9–8,1 ppm | 7 protons |

PHARMACOLOGICAL RESULTS

Table 2 shows the toxicity of certain products of this invention administered orally to mice. This toxicity is estimated by the calculation of the lethal dose of 50 (LD 50) which determines the fatal dose of the substance for 50% of the animals tested. This determination was effected in accordance with a modification of the method by Litchfield and Wilcoxon (J. Pharmacol. Exp. Therap. 1949, 96, 99–113). Also shown is LDO which is defined as the maximum dose of the substance which did not lead to any mortality of the animals subjected to the test.

Swiss mice without specific pathogenic organisms were kept in air conditioned rooms 24 to 48 hours before the start of the tests. They were divided into batches of 5 ♂ and 5 ♀. With the animals unfed for 24 hours, the substances were intragastically administered in suspension in 2% Tween 80 or in 6% gummy julep in a volume equivalent to 0.1 ml per 10 g of the weight of the animal.

After the treatment, the animals were observed for one hour and then every hour throughout the first day. They remained under observation for two weeks before being killed and subjected to an autopsy.

TABLE 2

| PRODUCT | LDO mg/kg | LD50 mg/kg |
|---|---|---|
| 1 | | ~ 2600 |
| 2 | ~ 1500 | ~ 2000 |
| 3 | 1000 – 2000 | ≧ 2000 |
| 4 | | ~ 2000 |
| 5 | > 2000 | > 2000 |
| 6 | 1000 – 2000 | ≧ 2000 |
| 7 | ~ 1000 | 70% deaths at 2000 |
| 8 | 750 – 1000 | ~ 1000 |
| 9 | 1000 – 2000 | > 2000 |
| 12 | | ~ 590 |
| 13 | ≧ 1000 | ≧ 3000 |
| 14 | > 2000 | |
| 15 | > 2000 | |
| 16 | > 2000 | |
| 17 | > 2000 | |
| 18 | > 2000 | |
| 19 | > 2000 | |
| 20 | > 2000 | |
| 21 | > 2000 | |
| 22 | > 2000 | |
| Niflumic acid | | ~ 350 |

All products were administered in gummy julep except No. 1 and No. 13 which were administered in Tween. The analgesic activity were determined in mice by utilizing as a nociceptive agent, phenylbenzoquinone (PBQ) (modification of the method by Siegmund and co-workers Proc. Soc. Exp. Biol. Med. 1957, 95, 729–31). The process consists of seeking a possible protection for the mouse vis-a-vis abdominal twisting and stretching of the hind legs induced by the parental injection of PBQ. 25 minutes after having orally administered the products to be tested in suspension in 2% Tween 80 or in 6% gummy julep, the PBQ solution was injected and the mice were observed after 5 minutes during the following 5 minutes. For certain products, AD 50 is presented as a measure of activity. These results are shown in Table 3.

TABLE 3

| PRODUCT | % ACTIVITY AT 200 mg/kg | AD 50 |
|---|---|---|
| 1 | 86 | 40 |
| 2 | 29 | |
| 3 | 29 | |
| 4 | 20 | |
| 5 | 42 | 270 |
| 6 | 25 | 420 |
| 7 | 81 | 80 |
| 8 | 54 | 180 |
| 9 | 100 mg/kg → 83 | 70 |
| 12 | 50 mg/kg → 61 | 45 |
| 13 | 150 mg/kg → 73 | 100 |
| 14 | 73 | 150 |
| 15 | 26 | |
| 16 | 100 mg/kg → 33 | |
| 17 | 28 | 420 |
| 18 | 44 | 260 |
| 19 | 300 mg/kg → 21 | 500 |
| 20 | 13 | 550 |
| 21 | 61 | 275 |
| 22 | 38 | 260 |
| Niflumic acid | | 17 |

All products were administered in gummy julep except No. 1 and No. 13 which were administered in suspension in Tween. The anti-inflammatory activity was determined by the carragenic test with male rats. Inflammation was induced by the injection of 0.1 ml of a 0.5% suspension of carragenine in a physiological serum into the muscular fasciculus of the metatarsal region of the hind leg of the animal. The substance to be tested was orally administered simultaneously with the carragenine. The edema was measured by phethysmography 1, 2, 3, 4, 5 and 6 hours after the administration of the carragenine. Table 4 shows the percentage of inhibitive activity as a function of the dose for certain products.

TABLE 4

| | % ACTIVITY | | | | | | | | ED 50 | |
|---|---|---|---|---|---|---|---|---|---|---|
| | 150 mg/kg | | 200 mg/kg | | 300 mg/kg | | 400 mg/kg | | mg/kg | |
| PRODUCT | 2H | 4H | 2H | 4H | 2H | 4H | 2H | 4H | 2H | 4H |
| 1 | 68 | 43 | | | | | 72 | 68 | 75 | 220 |
| 2 | | | | | | | | 20 | | |
| 3 | | | | 20 | | | | 21 | | |
| 4 | | | | 23 | | | | 13 | | |
| 5 | | | | 28 | | | | 17 | | |
| 6 | | | | 22 | | | | 3 | | |
| 7 | | | 19 | 20 | | | 23 | 25 | | |
| 8 | | | 68 | 66 | | | 74 | 48 | 180 | 230 |
| 9 | | | 29 | 39 | | | 71 | 60 | 220 | 240 |
| 12 | 33* | 17* | 43** | 28** | | | | | | |
| 13 | 77 | 50 | | | 76 | 55 | | | 230 | 210 |
| 14 | | | 63 | | 33 | | 79 | 63 | 175 | 260 |
| 15 | 15 | 21 | | | 15 | 4 | | | | |
| 16 | 12 | 10 | | | | | | | | |
| 17 | 27 | 17 | | | 29 | 8 | | | | |
| 18 | 16 | 6 | | | 22 | 0 | | | | |
| 19 | 21 | 23 | | | 26 | 27 | | | | |
| 20 | 16 | 3 | | | 10 | 13 | | | | |
| 21 | | | | | 44 | 43 | | | 400 | 500 |
| 22 | 35 | 31 | | | | | | | | |
| Niflumic acid | | | | | | | | | 34 | 125 |

*25 mg/kg All products were administered in gummy julep except No. 1 and
**50 mg/kg No. 13 which were administered in suspension in Tween.

Ulcerous activity was determined according to a modification of the method by Colot (Technical notions of general pharmacology, 1972) in the case of femal EOPS rats of approximately 150 g. The animals were left without absolutely any food, while the test products were orally administered on a daily basis in suspension in 2% Tween at a volume of 0.5 ml/100 g. The animals were killed under chloroform and the stomachs were removed. Ulcerous activity was established by means of an index taking into account the degree of ulceration and the percentage of animals effected.

In the table given below, a comparison is shown between the results obtained with niflumic acid and product No. 1.

| PRODUCT | | NUMBER OF DAYS | |
|---|---|---|---|
| | | 1 | 3 |
| 1 (250 mg/kg) | IA | 0 | 5 |
| | IC | 1.5 | 22 |
| | IT | | |
| Niflumic acid 83 mg/kg | IA | 8 | 16 |
| | IC | 380 | 206 |
| | IT | 388 | 222 |

IA: Acute ulceration index
IC: Ulceration index on the way of cicatrization
IT: Total index In view of their remarkable pharmacological properties, their slight toxicity and their excellent gastric tolerance (ulcerous activity very clearly inferior to that of the reference product: niflumic acid), the products of this invention can be very well utilized in human and veterinary therapeutics.

Their field of application pertains to all affections of an algique and inflammatory kind (in particular of an edematous kind). As an example, these products can be used therapeutically as follows:
  in rheumatology: inflammatory and degenerative rheumatism, articular and abarticular affections, gout . . .
  in traumalogy: sprains, fractures, luxations, tendinitis, lumbago.
  in surgery: pre- and post-operative pains
  in functional reeducation
  in dermato-phlebology: phlebitis, peri-phlebitis, varicose veins, cutaneous ulceration.

The compounds of the present invention can be employed to relieve the pain and inflammation which often accompany dental, O.R.L., visceral, vascular and neurologic diseases as well as cancer. The administration of these active substances in association with the usual excipients can be effected in an oral, rectal, or percutaneous manner in numerous pharmaceutical forms, such as pills, lozenges, gelatins, capsules, suppositories, ointments and gels.

In the oral administration of the compounds, a single dosage is normally of 100 to 500 mg. For suppositories a single dose ranges from 250 mg to 1g, while for ointments and gels, a single dosage ranges from 2 to 10%. The daily average dosology amounts to 2 to 4 oral administrations, one or two dosages for rectal administrations and 2 to 3 dosages for percutaneous applications.

In view of the perfect tolerance of these products and of their slight toxicity only, these doses can be exceeded in those cases where the symptomatology is particularly pronounced. The duration of the treatment is a function of the treated affection.

We claim:
1. A compound of the formula:

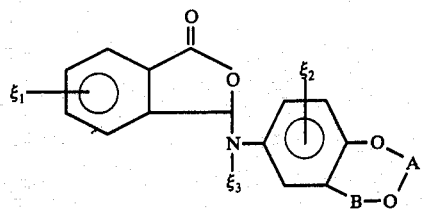

wherein $\xi_1$ is H or at least one substituent selected from the group consisting of OH, OMe, and OCOCH$_3$, and

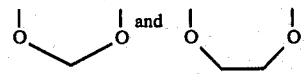

which are attached to two contiguous carbons of the benzene ring; $\xi_2$ is H or at least one substituent selected from the group consisting of C$_1$-C$_4$ lower alkyl, COOCH$_3$, COOH and the salts thereof of pharmacologically compatible bases; $\xi_3$ is H, C$_1$-C$_4$ lower alkyl, benzyl; A is

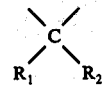

and R$_1$ and R$_2$ can be the same or different and are selected from the group consisting of hydrogen, C$_1$-C$_4$ lower alkyl, carbocyclic aryl, carbocyclicarylalkyl, and cycloalkyl and wherein R$_1$ and R$_2$ form, with the contiguous carbon atom, an alicyclic ring comprising at most 7 carbon atoms or A is

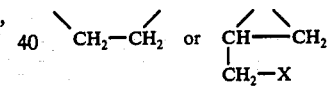

wherein X is halogen, OH, OCOCH$_3$, CH$_2$CH$_2$N⟨ ⟩,

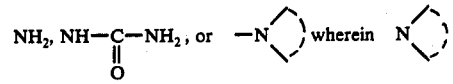

represents a secondary or tertiary acyclicamine or cyclicamine function; and B is a single bond or

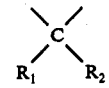

wherein R$_1$ and R$_2$ are as defined above with the proviso in the last case that $\xi_2$ be selected from the group consisting of H, C$_1$-C$_4$ lower alkyl and that A is

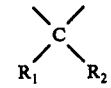

wherein R$_1$ and R$_2$ are as defined above.

2. The compound of claim 1 wherein

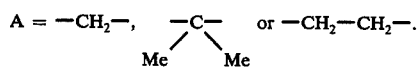

3. The compound of claim 1, wherein B is a single bond.

4. A compound of the formula

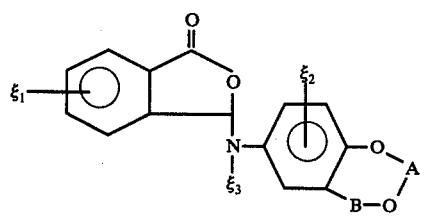

wherein $\xi_1$ is H or at least one substituent selected from the group consisting of OH, OMe and OCOCH$_3$, and

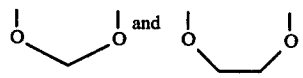

which are attached to two contiguous carbons of the benzene ring;

$\xi_2$ is H or at least one substituent selected from the group consisting of C$_1$–C$_4$ lower alkyl, COOCH$_3$, COOH and the salts thereof of pharmacologically compatible bases;

$\xi_3$ is H, C$_1$–C$_4$ lower alkyl, or benzyl; A is

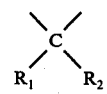

and R$_1$ and R$_2$ can be the same or different and are selected from the group consisting of hydrogen, C$_1$–C$_4$ lower alkyl, carbocyclicaryl, carbocyclicarylalkyl, and cycloalkyl and wherein R$_1$ and R$_2$ form, with the contiguous carbon atom, an alicyclic ring comprising at most 7 carbon atoms;

and B is a single bond.

5. The compound of claim 4, wherein A is —CH$_2$— or —C(Me)$_2$—.

6. A composition for the treatment of pain, which comprises:
an analgesically effective amount of the compound of claim combined with a pharmaceutically acceptable vehicle.

7. A composition for the treatment of inflammation, which comprises:
an anti-inflammatory effective amount of the compound of claim 1 combined with a pharmaceutically acceptable vehicle.

8. A composition for the treatment of pain, which comprises:
an analgesically effective amount of the compound of claim 4 combined with a pharmaceutically acceptable vehicle.

9. A composition for the treatment of inflammation, which comprises:
an anti-inflammatory effective amount of the compound of claim 4 combined with a pharmaceutically acceptable vehicle.

* * * * *